(12) United States Patent
Bouarab et al.

(10) Patent No.: US 7,041,485 B2
(45) Date of Patent: May 9, 2006

(54) METHOD FOR PREPARING FREE POLYUNSATURATED FATTY ACIDS AND THEIR OXIDATION METABOLITES

(75) Inventors: Kamal Bouarab, Sherbrook (CA); Jean-Pierre Salaun, Landeda (FR); Jean-Claude Yvin, Saint Malo (FR); Philippe Potin, Roscoff (FR)

(73) Assignee: Laboratoires Goemer S.A., Saint-Malo Cedex (FR)

( * ) Notice: Subject to any disclaimer, the term of this patent is extended or adjusted under 35 U.S.C. 154(b) by 62 days.

(21) Appl. No.: 10/630,359

(22) Filed: Jul. 30, 2003

(65) Prior Publication Data

US 2004/0209334 A1 Oct. 21, 2004

(51) Int. Cl.
*C12P 7/64* (2006.01)

(52) U.S. Cl. .................. 435/134; 435/41; 435/132; 208/311

(58) Field of Classification Search .................. 435/41, 435/132, 134, 257.1; 208/311
See application file for complete search history.

(56) References Cited

U.S. PATENT DOCUMENTS

| | | | |
|---|---|---|---|
| 5,338,673 A | | 8/1994 | Thepenier et al. |
| 5,552,307 A | * | 9/1996 | Kessler et al. ............. 435/171 |

FOREIGN PATENT DOCUMENTS

| | | |
|---|---|---|
| EP | 0 277 747 A2 | 8/1988 |
| WO | WO 99/15688 | 4/1999 |

OTHER PUBLICATIONS

Gerwick, WH, et al. Biologically active oxylipins from seaweeds. Hydrobiologia. 1993. 260-261: 653-65. CAPLUS Abstract.*

Bouarab, K., et al. Sulfated oligosaccharides mediate the interaction between a marine red alga and its green algal pathogenic endophyte. Plant Cell. 1999. 11(9): 1635-1650.*

Nakano, T., et al. Characterization of catalase from the seaweed Porphyra yezoensis. Plant Science. 1995. 104(2): 127-133. Abstract.*

Galland-Irmouli, AV, et al. One-step purification of R-phycoerythrin from the red macroalga Palmaria palmata using preparative polyacrylamide gel electrophoresis. Journal of Chromatography B. 2000. 739(1): 117-123. Abstract.*

Campbell, NA, ed. Biology, Third edition. 1993. Benjamin/Cummings Publishing Company, Inc. pp. 740-744.*

Ahern, Tim J., et al., "Arachidonic Acid Production by the Red Alga *Porphyridium cruentum*," Biotechnology and Bioengineering, vol. XXV, pp. 1057-1070, 1983.

Bouarab, Kamal, et al., "The *Chondrus crispus-Acrochaete operculata* Host-Pathogen Association, a Novel Model in Glycobiology and Applied Phycopathology," Journal of Applied Phycology, 13: pp. 185-193, 2001.

Tasende, M.G., "Fatty Acid and Sterol Composition of Gametophytes and Sporophytes of *Chondrus crispus* (Gigartinaceae, Rhodophyta)," Scientia Marina, 64 (4), pp. 421-426, 2000.

* cited by examiner

*Primary Examiner*—Francisco C. Prats
*Assistant Examiner*—Susan E. Fernandez
(74) *Attorney, Agent, or Firm*—McDonnell Boehnen Hulbert & Berhoff LLP

(57) ABSTRACT

The invention relates to a method for preparing free polyunsaturated fatty acids and their oxidation metabolites, wherein, successively, the production of polyunsaturated fatty acids and of their oxidation metabolites is stimulated, in a red alga, by the action of an elicitor which is peptide, lipid or saccharide in nature, and then the polyunsaturated fatty acids produced and also their oxidation metabolites are extracted.

3 Claims, No Drawings

METHOD FOR PREPARING FREE POLYUNSATURATED FATTY ACIDS AND THEIR OXIDATION METABOLITES

The invention relates to a method for preparing free polyunsaturated fatty acids and their oxidation metabolites.

It is more particularly directed toward the use of the method in accordance with the invention for preparing 12-hydroxyeicosatetraenoic acid or 12-HETE, and 11,12-epoxyeicosatrienoic acid or 11,12-EET, which are oxidation metabolites of arachidonic acid and which constitute important medicinal products in the sense that they restore, correct or modify certain organic functions in humans; these medicinal products are the subject of the patent application filed by the applicant company on the same date as the present application, under the title "novel medicinal product".

The invention is based on the result of studies carried out by the applicant company and which enabled it to find that it was possible to stimulate, using elicitors which are protein, lipid or saccharide in nature, the production of these metabolites in red algae, and more particularly *Chondrus crispus*, in the defense reactions of which they play a role which has not yet been elucidated, in the knowledge that it is already known that these metabolites are produced at the end of the cascade of arachidonic acid oxidation under the action of lypoxygenase for the first and under the action of a cytochrome P450 enzyme for the second.

It is to the applicant company's credit to have found that this stimulation in *Chondrus crispus* could advantageously be obtained using, as elicitors, components produced by the green alga *Acrochaete operculata*.

Once the stimulation has been produced, a result which is obtained in approximately 6 to 12 hours after inoculation of the elicitor on the substrate consisting of the red alga, the arachidonic acid and the metabolites produced are extracted from the *Chondrus crispus* plant tissue.

It ensues that, in the method in accordance with the invention for preparing free polyunsaturated fatty acids and their oxidation metabolites, the following are successively carried out, the release of polyunsaturated fatty acids and the production of their oxidation metabolites are stimulated, in a red alga, by the action of an elicitor which is peptide, lipid or saccharide in nature, and then the released polyunsaturated fatty acids and also their oxidation metabolites are extracted.

According to an advantageous embodiment of the method in accordance with the invention, the stimulation of the release of the polyunsaturated fatty acids and of the production of their oxidation metabolites is obtained, in the case of the red alga *Chondrus crispus*, by elicitation under the action of components of the green alga *Acrochaete operculata*.

According to another advantageous embodiment of the method in accordance with the invention, the elicitation is carried out by making use of an extract of *Acrochaete operculata*, obtained by aqueous treatment under cold conditions or under hot conditions of alga ground material.

Consequently, with the intention of preparing polyunsaturated fatty acids and their oxidation metabolites, including in particular 12-HETE and 11,12-EET, in accordance with the invention, the following procedure, or an equivalent one, is carried out.

First of all, thalluses from *Chondrus crispus* are cultured.

To do this, these thalluses are cultured [in particular using a haploid strain (gametophytes) identified by JC002PC-6 and sent by the laboratory of Professor Juan Correa of the Faculty of Biological Sciences, Catholic University, Santiago, Chile] in a culture medium referred to as SFC and prepared by adding, to 1 litre of seawater, filtered with a 0.2 µm filter, a 2 ml amount of each one of the five solutions identified below and prepared as indicated:

1. Iron-based solution 367 mg/l of ferric sodium ethylenediaminetetraacetic acid salts are dissolved in distilled water.

2. Phosphate-based solution.

50 mM ($NaH_2PO_4.H_2O$) is prepared in distilled water.

3. Nitrate-based solution.

1 M $NaNO_3$ is prepared in distilled water.

4. Metal-based solution.

Solutions of 14 mg/ml of ($MnCl_2.4H_2O$), of 1 mg/ml of $ZnCl_2$, of 47 µg/ml of ($CoCl_2.6H_2O$) and of 0.04 µg/ml of ($CuCl_2.2H_2O$) in distilled water are prepared separately; a 50 ml volume of each one of these solutions is added to a solution of $Na_2EDTA$ (4.36 g/l); the mixture is boiled for 10 minutes, 1 liter of distilled water is added, and the pH is adjusted to 7.5 before filtering with a 0.2 µm filter.

5. Vitamin-based solution.

Solutions of biotin (0.5 mg/l), of folic acid (1 mg/l), of thiamine B1 (1.5 mg/l) and of B12 (0.5 mg/l) in distilled water are prepared separately; 1.25 ml of each one of these solutions are added to 250 ml of seawater filtered with a 0.2 µm filter.

Isolates of *Acrochaete operculata* (in particular isolates obtained from the laboratory of Professor Juan Correa and which consist of single-alga cultures established from *Chondrus crispus* thalluses naturally infected with this endophyte, harvested in Canada in 1987 and identified by KH 040687-1-1) are, moreover, cultured, again using the medium defined above.

The two cultures are maintained at 15° C. with a photoperiod of 16/8 (day/night) and a light flux of 40 µmol m-2 s-1.

The medium from each culture is renewed every week.

After culturing for 4 months, when the *Acrochaete operculata* biomass reaches an amount of approximately 5 g of drained fresh algae per 5 liters of culture medium, a 1.5 g fraction of algae is removed, filtered on Whatman 3MM paper and drained by pressing.

This biomass is then frozen in liquid nitrogen and stored in a freezer at −80° C.

To prepare the acellular extracts of *Acrochaete operculata*, the abovementioned 1.5 g fraction of *Acrochaete operculata* frozen in liquid nitrogen is used, it is reduced to powder in liquid nitrogen and, after evaporation of the nitrogen, the powder is taken up in 1 ml of extraction buffer consisting of 0.5 M Tris HCl, pH 6.5, 50 mM of NaCl and 10 mM of $MgCl_2$.

The extraction can be carried out under cold conditions or under hot conditions at 100° C. for 15 minutes.

After centrifugation at 12 000 g for 30 minutes, the supernatant is recovered.

This supernatant constitutes the extract used as elicitor.

The *Chondrus crispus* culture, which was referred to above, is continued for 4 to 8 months.

At the end of this culturing, a 500 mg (fresh weight) sample of gametophytes is removed.

This sample is used for the elicitation.

For this elicitation, the 500 mg of gametophytes are incubated for 1 hour in 10 ml of seawater, filtered with a 0.2 µm filter, in the presence of a 70 µl amount of the abovementioned *Acrochaete operculata* extract.

Activation of the phospholipases is thus induced, which phospholipases release free polyunsaturated fatty acids, including arachidonic acid, and also the lipoxygenases and the cytochrome P450 under the respective action of which the metabolites 12-HETE and 11,12-EET are formed from the arachidonic acid.

Once the incubation has finished (the end of the incubation can be controlled by freezing the algae in liquid nitrogen), the fatty acids and the metabolites formed are recovered by extraction.

To do this, an aqueous extraction of the red alga ground in liquid nitrogen, followed by an extraction with organic solvent, can be successively carried out.

First of all, an aqueous extract of the gametophytes which were subjected to the elicitation with the *Acrochaete operculata* extract is prepared.

To do this, a 5 g amount of the gametophyte culture incubated with the extracts of the green alga *Acrochaete operculata* is subjected to grinding with liquid nitrogen.

The product resulting from this grinding is suspended in 20 ml of a 50 mM Tris-HCl buffer, at pH 9.5, containing 500 mM of KCl and 10 mM of β- mercaptoethanol.

After homogenization by slow stirring in ice, the extract is centrifuged at 12 000 g for 10 minutes, and the proteins contained in the supernatant are then assayed by the Bradford method (1976). The assaying reagent used is a commercial product based on a dye, Coomassie blue, and sold under the Bio-Rad protein assay trademark; it is an anionic form of the dye which preferentially attaches to the proteins by interaction with their cationic groups.

The samples are first of all solubilized in a buffer of 10 mM $MgCl_2$, 50 mM NaCl, 1 mM perfablock, 50 mM Tris HCl, at pH 7.5, and centrifuged for 10 minutes at 12 000 g.

200 µl of the abovementioned Bio-Rad reagent are added to 800 µl of dilute extract containing between 1 and 10 µg of proteins, and the optical density is measured at 595 nm using a spectrophotometer.

The calibration is carried out using a standard range produced with bovine serum albumin.

A soluble protein extraction yield is thus determined.

It is from the abovementioned aqueous extract that the fatty acids and their metabolites are recovered.

This extract, which contains 24 mg of proteins, is diluted with 100 mM Tris buffer, pH 8.5, so as to obtain a volume of 40 ml.

The metabolites are extracted twice with 60 ml of diethyl ether.

The organic phase is evaporated to dryness under a stream of nitrogen and the residues are redissolved in absolute ethanol.

An aliquot portion is evaporated and redissolved in 100 µl of acetonitrile.

A 40 µl amount is injected for analysis by RP-HPLC coupled to an APCI-ESI-MS detector for identification based on comparison of the mass spectrum of the metabolite with that of an authentic standard and quantification by calibrating with known amounts of the fatty acid metabolites such as 12-HETE and 11,12-EET.

The final preparation contains 1.5 µg of 12-HETE and an amount of 11,12-EET of less than or equal to 0.5 µg.

The final yield for the preparation is 0.3 mg of 12-HETE and 0.1 mg of 11,12-EET per kilogram of fresh alga.

These metabolites are stable in ethanol for several months and are conserved at −20° C.

Other metabolites, including hydroperoxides (12-HPETE, 13-HPOTE, 13-HPODE) or keto alcohols or epoxys and hydroxylated derivatives of arachidonic acid, linolenic acid or linoleic acid, are also identified and, given their biological activities on animal or plant systems, these compounds, obtained using the method which is the subject of the present invention, might give rise to novel applications.

The invention claimed is:

1. A method for preparing 12-hydroxyeicosatetraenoic acid or (12-HETE), 11,12-epoxyeicosatrienoic acid (11,12-EET), which are oxidation metabolites of arachidonic acid, said method comprising culturing thalluses of the red algae *Chondrus crispus*, culturing isolates of the green algae *Acrochaete operculata* to obtain an *Acrochaete operculata* biomass, preparing an extract from said *Acrochaete operculata* biomass, incubating the result of the culture of the *Chondrus crispus* thalluses with the extract obtained from the *Acrochaete operculata* biomass, centrifugating the result of the incubation and obtaining a supernatant removing the supernatant and recovering therefrom the 12-HETE and the 11,12-EET.

2. A method according to claim 1 for preparing 12-hydroxyeicosatetraenoic acid or (12-HETE), 11,12-epoxyeicosatrienoic acid (11,12-EET), which are oxidation metabolites of arachidonic acid, said method comprising culturing thalluses of the red algae *Chondrus crispus*, culturing isolates of the green algae *Acrochaete operculata* to obtain an *Acrochaete operculata* biomass, subjecting said *Acrochaete operculata* biomass to freezing in liquid nitrogen, thus providing a frozen biomass of *Acrochaete operculata*, maintaining the frozen biomass of *Acrochaete operculata* in the liquid nitrogen and reducing it to powder, evaporating the liquid nitrogen, taking up the powder in an extraction buffer to obtain a mixture of the powder and the extraction buffer and carrying out an extraction, subjecting to centrifugation the mixture obtained by taking up the powder in the extraction buffer, providing thus a supernatant and recovering the supernatant, removing a sample of gametophytes from the culture of thalluses of *Chondrus crispus*, incubating the said sample of gametophytes with said supernatant, thus activating phospholipases which release arachidonic acid as well as lipoxygenases and cytochrome P450 under the respective action of which 12-HETE and 11,12-EET are formed from the arachidonic acid, extracting 12-HETE and 11,12-EET from the incubated sample of gametophytes with diethyl ethers.

3. A method according to claim 1 for preparing 12-hydroxyeicosatetraenoic acid or (12-HETE), 11,12-epoxyeicosatrienoic acid (11,12-EET), which are oxidation metabolites of arachidonic acid, said method comprising culturing thalluses of the red algae *Chondrus crispus*, culturing isolates of the green algae *Acrochaete operculata* to obtain an *Acrochaete operculata* biomass, subjecting said *Acrochaete operculata* biomass to freezing in liquid nitrogen, thus providing a frozen biomass of *Acrochaete operculata*, maintaining the frozen biomass of *Acrochaete operculata* in the liquid nitrogen and reducing it to powder, maintaining the frozen biomass of *Acrochaete operculata* in the liquid nitrogen and reducing it to powder,
evaporating the liquid nitrogen,
taking up the powder in an extraction buffer to obtain a mixture of the powder and the extraction buffer and carrying out an extraction,
subjecting to centrifugation the mixture obtained by taking up the powder in the extraction buffer, providing thus a supernatant and recovering the supernatant,
removing a sample of gametophytes from the culture of thalluses of *Chondrus crispus*,
incubating the sample of gametophytes with the said supernatant, thus activating phospholipases which release arachidonic acid, as well as lipoxygenases and cytochrome P450 under the respective action of which 12-HETE and 11,12-EET are formed from the arachidonic acid,
grinding in liquid nitrogen the sample of incubated gametophytes,
suspending in a Tris-HCL buffer the product resulting from the grinding,
centrifugating the suspended product providing a supernatant,
recovering the supernatant and diluting it with Tris buffer,
extracting 12-HETE and 11,12-EET from the diluted supernatant with diethyl ether.

\* \* \* \* \*